US006130227A

United States Patent [19]

Merlini et al.

[11] Patent Number: 6,130,227

[45] Date of Patent: Oct. 10, 2000

[54] 7-SUBSTITUTED CAMPTOTHECIN DERIVATIVES AND METHODS FOR INHIBITING THE GROWTH OF TUMOR CELLS THEREWITH

[75] Inventors: Lucio Merlini; Sergio Penco; Franco Zunino, all of Milan, Italy

[73] Assignee: Istituto Nazional per Lo Studio e la Cura Dei Tumori, Milan, Italy

[21] Appl. No.: 09/125,512

[22] PCT Filed: Feb. 19, 1997

[86] PCT No.: PCT/EP97/00786

§ 371 Date: Aug. 20, 1998

§ 102(e) Date: Aug. 20, 1998

[87] PCT Pub. No.: WO97/31003

PCT Pub. Date: Aug. 28, 1997

[30] Foreign Application Priority Data

Feb. 23, 1996 [IT] Italy ................................ MI96A0338

[51] Int. Cl.[7] .................... A61K 31/4761; C07D 471/14; C07D 471/16

[52] U.S. Cl. ............................... 514/283; 546/51; 546/48

[58] Field of Search ......................... 546/51, 48; 514/283

[56] References Cited

U.S. PATENT DOCUMENTS

| | | | |
|---|---|---|---|
| 4,399,282 | 8/1983 | Hausheer et al. | 548/48 |
| 5,859,023 | 1/1999 | Hausheer et al. | 514/283 |
| 5,910,491 | 6/1999 | Hausheer et al. | 514/63 |

FOREIGN PATENT DOCUMENTS

| | | |
|---|---|---|
| 0 088 642 | 9/1983 | European Pat. Off. . |

*Primary Examiner*—Alan L. Rothman
*Assistant Examiner*—Rita Desai
*Attorney, Agent, or Firm*—Birch, Stewart, Kolasch & Birch, LLP

[57] ABSTRACT

20S-Camptothecin derivatives in which the 7-position bears as a substituent —CN, $—CH(CN)R_4$, $—CH{=}C(CN)R_4$, $—C({=}NOH)NH_2$, $—C({=}NH)NH_2$, $—CH{=}C(NO_2)R_4$, $—CH(CN)R_5$, $—CH(CH_2NO_2)R_5$, tetrazol-5-yl, 4,5-dihydrooxazol-2-yl, or 1,2,4-oxadiazolin-3-yl-5-one. These compounds are active as topoisomerase I inhibitors, and can be used as antitumor drugs.

15 Claims, No Drawings

7-SUBSTITUTED CAMPTOTHECIN DERIVATIVES AND METHODS FOR INHIBITING THE GROWTH OF TUMOR CELLS THEREWITH

CROSS-REFERENCE TO RELATED APPLICATION

This application is a 371 of PCT/EP97/00786, filed Feb. 19, 1997.

The present invention relates to derivatives of camptothecin, to a process for their preparation, to their use as active ingredients for the preparation of medicament useful in the treatment of tumors, and to pharmaceutical preparations containing them.

The antitumoral agent 20S-camptothecin, of formula

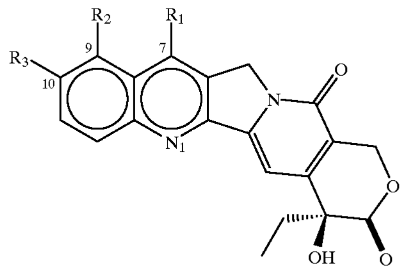

where $R_1$, $R_2$ and $R_3$ are hydrogen, discovered in 1966 by M. E. Wall et al. (J. Amer. Chem. Soc. 88, 3888–90 (1966), after a preliminary clinical evaluation was withdrawn as a therapeutic agent because of its toxicity for man and of its low solubility, which made difficult its administration in suitable pharmaceutical preparations. The attention of academic and industrial researchers was then devoted to the synthesis of camptothecin analogues with improved therapeutic profile. Two out of the numerous analogues described by the above drawn formula, namely Topotecan, where $R_1$ is hydrogen, $R_2$ is the —$CH_2$—$NH(CH_3)_2$ group, $R_3$ is OH, and CPT-11, where $R_1$ is ethyl, $R_2$ is hydrogen, and $R_3$ is

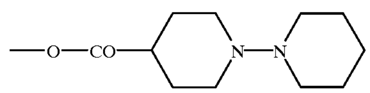

have recently become available to the oncologist for the treatment of some tumors (J. of Clinical Oncology, 10, 1775–80 (1992); J. of the National Cancer Inst. 85, 271 (1993). Other derivatives presently in clinical trials are 9-aminocamptothecin and the analogue of formula:

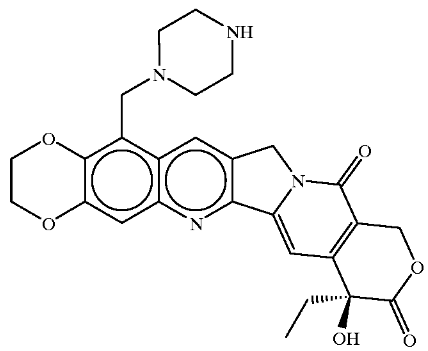

(Cancer Treatment Reviews 20, 73–96 (1994)).

Most synthetic efforts have been devoted to the introduction of suitable substituents to overcome the problem of the scarce water solubility that characterizes this class of compounds, and that can lead to difficulties in their formulation and to unpredictable plasma levels of the drug. Moreover, the persistence of the lactone ring in closed form is an important factor for the antitumor efficacy.

The relevance of this class of compounds is also due to their peculiar mechanism of action: in fact they display their antitumoral effects by inhibiting topoisomerase I, an enzyme that regulates DNA topology and therefore plays a critical role in essential cellular pathways such as DNA replication, transcription, recombination and repair (C. Capranico and F. Zunino, Current Pharm. Design, 1, 1–14 (1995). The need for new drugs effective against colorectal, non small cell lung carcinoma, ovarian tumors and prostatic carcinoma, still little responsive to chemiotherapeutic treatment, makes rewarding the search for new camptothecin derivatives with improved pharmacological properties.

It has now been found that derivatives of camptothecin and of 10-hydroxycamptothecin carrying substituents at carbon C-7 exhibit antitumor activity and possess favourable physico-chemical properties that allow their formulation in suitable pharmaceutical compositions.

The present invention comprises compounds of formula (I), (I)

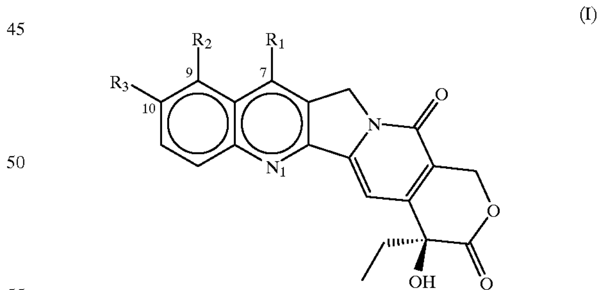

wherein:

$R_1$ is —CN, —CH(CN)—$R_4$, —CH=C(CN)—$R_4$, —$CH_2$—CH(CN)—$R_4$, —C(=NOH)—$NH_2$, —C(=NH)—$NH_2$, —CH=C($NO_2$)—$R_4$, —CH(CN)—$R_5$, —CH($CH_2NO_2$)—$R_5$; 5-tetrazolyl, 2-(4,5-dihydrooxazolyl), 1,2,4-oxadiazolin-3-yl-5-one;

$R_2$ is hydrogen;

$R_3$ is hydrogen, $OR_6$;

$R_4$ is hydrogen, $C_1$–$C_6$ linear or branched alkyl, CN, $COOR_7$;

$R_5$ is hydrogen, $OR_8$;

$R_6$ is hydrogen, $C_1$–$C_6$ linear or branched alkyl, ($C_6$–$C_{12}$) aryl ($C_1$–$C_4$) alkyl, ($C_1$–$C_4$) alkoxy ($C_1$–$C_4$) alkyl, ($C_1$–$C_4$) alkyl ($C_6$–$C_{12}$) aryl, ($C_6$–$C_{12}$) aryl ($C_2$–$C_4$) acyl, ($C_2$–$C_4$) acyl, amino ($C_1$–$C_4$) alkyl, amino ($C_2$–$C_4$) acyl, glycosyl;

$R_7$ is hydrogen, $C_1$–$C_6$ linear or branched alkyl, ($C_6$–$C_{12}$) aryl ($C_1$–$C_4$) alkyl, ($C_1$–$C_4$) alkoxy ($C_1$–$C_4$) alkyl, ($C_1$–$C_4$) alkyl ($C_6$–$C_{12}$) aryl;

$R_8$ has the same meanings of $R_6$, independently of the latter; their $N_1$-oxides, their isomers, diastereoisomers, enantiomers and mixtures thereof, as well as their metabolites, in particular active metabolites.

The present invention includes also the pharmaceutically acceptable salts.

The present invention includes the use of compounds of formula (I) as active ingredients for the preparation of medicaments, in particular medicaments useful for the treatment of tumors.

The present invention includes pharmaceutical compositions containing compounds of formula (I) as active ingredients.

The present invention includes a process for the preparation of compounds of formula (I).

The present invention includes the use of compounds of formula (I) wherein $R_1$ is CN as intermediates for the preparation of other compounds of formula (I), wherein $R_1$ is —C═(NOH)—$NH_2$, —C(═NH)—$NH_2$, 5-tetrazolyl, 2-(4,5-dihydrooxazolyl).

Examples of $C_1$–$C_6$ alkyl are methyl, ethyl, propyl, isopropyl, butyl, sec-butyl, tert-butyl, pentyl, 2-methylbutyl, isopentyl, hexyl, 3-methylpentyl, 2-ethylbutyl.

Example of ($C_6$–$C_{12}$) aryl ($C_1$–$C_4$) alkyl are: benzyl, mono or polysubstituted $C_1$–$C_6$ alkyl benzyl, α- or β-phenylethyl, mono- or poly $C_1$–$C_4$ alkyl-substituted α- or β-phenylethyl, mono or poly $C_1$–$C_4$ alkyl-substituted α-, β- or γ-phenylpropyl, α- or β-napthylmethy1, mono or poly $C_1$–$C_2$ alkyl substituted α- or β-napthylmethyl.

Examples of ($C_1$–$C_2$) alkoxy ($C_1$–$C_4$) alkyl are methoxymethyl, ethoxyethyl, ethoxymethyl, propoxyethyl, butoxyethyl.

Examples of ($C_1$–$C_4$) alkyl ($C_6$–$C_{12}$) aryl are tolyl, xylyl, ethylphenyl, isopropylphenyl, terbutylphenyl, methylnaphthyl.

Examples of ($C_6$–$C_{12}$) aryl ($C_2$–$C_4$) acyl are phenylacetyl, naphthylacetyl, 2-phenylpropionyl, 3-phenylpropionyl, 2-, 3- or 4-phenylbutirryl, mono, di- or tri ($C_1$–$C_4$) alkyl substituted phenylacetyl.

Examples of $C_2$–$C_4$ acyl are acetyl, propionyl, butirryl and their isomers.

Examples of amino ($C_1$–$C_4$) alkyl and amino ($C_2$–$C_4$) acyl are $C_1$–$C_4$ alkyl and $C_2$–$C_4$ acyl wherein the amino substituents can be in any position of the carbon chain.

Examples of pharmaceutically acceptable salts are:

in case of a basic nitrogen atom, salts with pharmaceutically acceptable acids, both inorganic and organic, such as hydrochloric acid, sulfuric acid, acetic acid, in case of an acid group, such as —COOH, salts with pharmaceutically acceptable bases, both inorganic and organic, such as alkali and alkaline earth hydroxides, ammonium hydroxide, amines.

The compounds of formula (1) may be in the form of pharmaceutically acceptable salts and/or of $N_1$-oxides. A list of preferred groups of compounds is given below.

A first group of preferred compounds includes compounds of formula (I) where $R_3$ is hydrogen.

A second group of preferred compounds includes compounds of formula (I) where $R_3$ is $OR_6$ and $R_6$ is as above defined.

A third group of preferred compounds includes compounds of formula (I) wherein $R_1$ is CN, $R_3$ is hydrogen or $OR_6$, and $R_6$ is as above defined.

A fourth group of preferred compounds includes compounds of formula (I) wherein $R_1$ is CH(CN)—$R_4$, wherein $R_4$ is preferably CN or $COOR_7$, $R_7$ being as above defined.

A fifth group of preferred compounds includes compounds of formula (I) wherein $R_1$ is CH(═NOH)$NH_2$, $R_3$ is $OR_6$, as defined above.

A sixth group of preferred compounds includes compounds of formula (I) wherein $R_1$ is CH(═NH)$NH_2$, $R_3$ is $OR_6$, as defined above.

A seventh group of preferred compounds includes compounds of formula (I) wherein $R_1$ is CH═C(CN)$R_4$, wherein $R_4$ is preferably CN or $COOR_7$, $R_7$ being as above defined, in particular $R_4$ is CN, $R_2$ and $R_3$ are hydrogen.

An eigth group of preferred compounds includes compounds of formula (I) wherein $R_1$ is CH($CH_2NO_2$)$R_5$, $R_5$ is $OR_8$ according to the above definitions.

A ninth group of preferred compounds includes compounds of formula (I) wherein $R_1$ is CH═C($NO_2$)—$R_4$, wherein $R_4$ is H, $R_3$ is $OR_6$ according to the above definitions.

Compounds of formula (I) particularly preferred are those where $R_1$ is CN or CH═C$(CN)_2$ or —$CH_2$CH(CN)—$R_4$ and $R_2$ and $R_3$ are hydrogen.

The compounds of formula (I) can be obtained starting from camptothecin-7-methanol (II, $R_1$=$CH_2OH$, $R_2$=H, $R_3$=H) or from 10-hydroxycamptothecin-7-methanol (II, $R_1$=$CH_2OH$, $R_2$=H, $R_3$=OH), or from camptothecin-7-aldehyde (II, $R_1$=CHO $R_2$=H, $R_3$=H), or from camptothecin-N-oxide, all compounds available as described by Sawada et al. Chem. Pharm. Bull. 39, 2572 (1991).

(II)

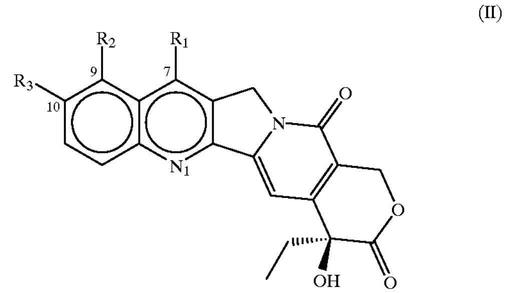

Compounds of formula (I) where $R_1$=—CN are prepared by a process including the oxidation of compounds of formula (II, $R_1$=—$CH_2OH$) to compounds of formula (II, $R_1$=—CHO) with known methods of oxidation of alcohols to aldehydes, such as Moffatt or Swern oxidation, or with iodosobenzoic acid in dimethylsulfoxide (Frigerio et al., J. Org. Chem. 60, 7272–6 (1995), or by acid treatment as described by Sawada et al. (Chem. Pharm. Bull. 39, 2572 (1991)), then treatment of these aldehydes with hydroxylamine to give the corresponding oximes, followed by heating the oxime with formic acid and sodium formate, or by other known methods of conversion of aldehydes into nitrites.

Compounds of formula (I, $R_1$=—CN, $R_1$=—CH(CN)—$R_4$) can also be obtained by reaction of N-oxides of camptothecin, for example those described by Sawada et al. (Chem. Pharm. Bull. 39, 2572 (1991), with potassium cyanide or trimethylsilylcyanide, or with malononitrile or esters of cyanoacetic acid respectively (as described in A. Albini and S. Pietra, Heterocyclic N-Oxides, CRC, 1991, p. 165), or by reaction of compounds of formula (II, $R_1$=—$CONH_2$)

by known methods of dehydration of amides to nitriles, or by other methods suitable for the preparation of quinoline-4-carbonitriles.

Aminohydroxyimines (I, $R_1$=—C(=NOH)—$NH_2$) are obtained by reaction of the corresponding nitrites (I, $R_1$=—CN) with hydroxylamine (F. Eloy and R. Lenaers, Chem. Rev. 61, 157 (1961)). The aminohydroxyimines can be reduced to the corresponding amidines (I, $R_1$=—C(=NH)—$NH_2$) by catalytic hydrogenation, preferably with Nickel-Raney as a catalyst (F. Eloy and R. Lenaers, ibid. p. 166). The same amidines can also be obtained from nitrites (I, $R_1$=—CN) with known methods of conversion of nitrites to amidines, such as reaction with HCl and an alcohol, followed by treatment with ammonia or an ammonium salt, or from amides (II, R=—$CONH_2$) with triethyloxoniumfluoborate (A. I. Meyers et al. Tetrahedron 39, 1991 (1983)).

Compounds of formula (I, $R_1$=—CH=C(CN)—$R_4$) are prepared for example by reaction of the aldehydes (II, $R_1$=—CHO) with malononitrile or with esters of malonic or cyanoacetic acid with or without the presence of organic or inorganic bases, or by reaction of the aldehydes or ketones (II, $R_1$=—CHO or —CO-alkyl) with suitable ylides or anions of phosphonates, according to Wittig or Wadsworth-Emmons reactions. If desired, the compounds of formula (I, $R_1$=—C=C(CN)—$R_4$) can be hydrogenated in the presence of a catalyst, such as Pd, or Pt or Ni, to the corresponding compounds of formula I ($R_1$=$CH_2CH(CN)R_4$).

Compounds of formula (I, $R_1$=—CH(CN)—$R_4$), —CH($CH_2NO_2$)—$R_5$), where $R_5$ is OH, can be prepared by reaction of the aldehydes (II, $R_1$=—CHO) with potassium or sodium cyanide or trimethylsilylcyanide, and, respectively, with nitromethane in the presence of an organic or inorganic base.

Compounds of formula (I, $R_1$=—CH=CH($NO_2$)—$R_4$) are obtained by acid treatment of compounds wherein $R_1$ is —CH($CH_2NO_2$)—$R_5$.

If desired, compounds of formula (I, $R_1$=—CN) can be converted, by known suitable methods, into compounds of formula (I), where $R_1$ is a heterocyclic ring, preferably 2-(4,5-dihydrooxazole) (J. F. Bower et al., J.Chem.Soc. Perkin Trans. 1, 333 (1996)) or 5-tetrazole (Duncia et al. J. Org. Chem. 56, 2395 (1991)).

Compounds of formula (I, $R_1$=1,2,4-oxadiazolin-3-yl-5-one) are obtained from the corresponding amidines.

N-oxides of compounds of formula (I) are prepared according to known methods of oxidation of heteroaromatic nitrogen, preferably by oxidation with acetic or trifluoroacetic acid and hydrogen peroxide, or by reaction with organic peroxyacids (A. Albini and S. Pietra, Heterocyclic N-Oxides, CRC, 1991).

Pharmaceutically acceptable salts of compounds of formula (I) can be obtained according to literature methods.

The compounds described in the present invention exhibit a potent antiproliferative activity and possess physicochemical properties that make them suitable to be included in pharmaceutically acceptable compositions.

The cytotoxic activity of the compounds of the present invention has been tested in cellular systems of human tumor cells, using the antiproliferative test as a method of evaluation of the cytotoxic potential. The method consists in the determination of the number of 72-hrs surviving cells after 1 hour of exposure to the cytotoxic agent. The cytotoxic activity of the compounds of the present invention has been compared to that of i) topotecan as reference agent among the inhibitors of DNA topoisomerases I; ii) doxorubicin, standard antitumor agent, one of the most effective amomg those employed in the clinical therapy of tumors. The results reported in Table 1 indicate that the compound of formula (I) described in the Example 1 below (I, $R_1$=—CN, $R_2$=H, $R_3$=H) and the compound of formula (I) described in the Example 4 below (I, $R_1$=CH=C(CN)—$R_4$, $R_4$=CN, $R_2$=H, $R_3$=H) exhibit a cytotoxic activity greater than that of the reference compounds in a non-small cell lung carcinoma system (non SCLC) (H-460), intrinsecally resistant to cytotoxic therapy and only moderately responsive to topoisomerase I inhibitors, in spite of overexpression of the target enzyme.

TABLE 1

Cytotoxic activity of camptotecin analogs in a panel of human tumor cells (1 h exposure to drug; antiproliferative activity was determined 72 h after drug exposure)

| Cell line | Example 1 | Example 4 | Topotecan | Doxorubicin |
|---|---|---|---|---|
| H460 (lung carcinoma non-SCLC) | 0.08 ± 0.02 | 0.19 | 0.34 ± 0.04 | 0.09 |
| H460/TPT | 12 ± 2 | | 80 | |
| GBM (glioblastoma) | 2.7 | | 1.2 | |

Moreover, the compound of Example 1 shows appreciable efficacy in the treatment of a cellular line (H460/TPT), selected after prolonged exposure to Topotecan and characterized by high degree of strong resistance to topotecan. As H460 line expresses high levels of topoisomerase I, the improved cytotoxicity of the compound reported in Example 1 below in the treatment of this tumor cell line indicates an improved specificity of the compound toward the cellular target. This interpretation is supported by the reduced efficacy of these compounds on GBM cellular line, that is rather resistant to these inhibitors, due to the low expression of topoisomerase I.

A preclinical efficacy study was designed to evaluate the antitumor activity of the compounds of the present invention in comparison with topotecan (a first generation camptothecin already in clinical trials) as reference drug. The human tumor line NCI-H460, a non small cell lung carcinoma, was chosen because of the high expression of topoisomerase I, the known target of camptothecin drugs. This tumor model is relatively resistant to in vivo treatment with conventional cytotoxic agents (e.g., doxorubicin, cisplatin). Tumor cells were injected i.p. into nude mice ($2.5\times10^6$ cell/mouse) of about 10 weeks and 3 days later the drugs were injected in the peritoneal cavity (10 ml/kg b.w.) to allow a direct contact of the drugs with tumor cells. Both topotecan and the compound of formula (I) described in Example 1 below, were delivered q4dx4 times. This schedule has been reported as optimal for camptothecin drugs in other preclinical studies. Mice were observed daily for death. The antitumor activity of the drugs was expressed as T/C %, i.e. the ratio between the median survival time of the drug-treated mice (T) and survival of the control untreated mice (C)×100. Treated mice, dead before the first control mouse or shortly after treatment with reduced body weight, were considered dead for drug toxicity. Mice still alive over 100 days after tumor cell inoculum were considered as long-term survivors (LTS). (The second experiment is still going and LTS are considered over 70 days). The results of two independent experiments are reported in Table 2.

TABLE 2

Efficacy of CPT 83 in the treatment of NCI-H460 human lung tumor xenograft growing i.p.
Treatment i.p. q4d × 4 times, starting from day 3 after tumor cell transplantation.

| Drug | mg/kg | % T/C | No. of toxic/ total no. mice | LTS (100 days) |
|---|---|---|---|---|
| Experiment 1 | | | | |
| Example 1 | 6.6 | 157 | 0/8 | 2/8 |
| | 10 | 258 | 0/8 | 3/8 |
| Topotecan | 10 | 215 | 0/8 | 2/8 |
| Experiment 2 | | | | |
| Example 1 | 10 | 233 | 0/7 | 1/7 |
| | 12 | 200 | 0/7 | 1/7 |
| | 14.4 | 277 | 1/7 | 2/7 |
| Topotecan | 10 | 261 | | 1/7 |
| | 12 | 77 | 4/7 | 0/7 |
| | 14.4 | 77 | 5/7 | 0/7 |

The compound of Example 1 according to the present invention, coded as CPT83, was highly effective in increasing survival time of i.p. tumor bearing mice, being T/C % values higher than 200 at all doses tested. As regard to drug toxicity, only 1 mouse died at the dose of 14.4 mg/kg×4 (total cumulative dose: 49.6 mg/kg). Drug efficacy of CPT83 was superior to that of topotecan in the experiment 1 under conditions in which tumor cells caused a delayed death (slowly-growing tumor). Using a rapidly growing tumor (experiment 2) the efficacy of CPT83 was comparable to that of topotecan in terms of T/C %. However, in both experiments a higher rate of long term survivors (LTS, i.e. cured animals) was found in CPT83-treated groups. This finding reflects a promising therapeutic profile related to an improved therapeutic index. The potential therapeutic advantage of CPT83 is also emphasized by its good activity in the treatment of a slowly growing tumor, which is more representative of growth in clinical setting. In conclusion, on NCI-H460 tumor xenograft, CPT83 has a comparable activity and a better tolerability than topotecan.

The compounds of the present invention show particularly advantageous properties, which can be summarized in the following points:

1. enhanced specifity for the cellular target and therefore for tumor cells expressing high levels of topoisomerase I. This possibility is supported by an increased sensivity of H460 tumor cells which are known to have high topoisomerase I levels. Indeed, this selectivity is lost in a cell line (GMB) characterized by low level of target expression.
2. The activity is apparently less dependent on the proliferation rate of the tumor than that of topotecan, as suggested by in vivo experiments and by appreciable activity against H460/TPT cell line characterized by a very slow proliferation. This profile of activity may have clinical implications, since slow growth is typical of human solid tumors.
3. The in vitro cytotoxic potency is not associated with an increased toxicity in vivo, thus allowing the use of a wide range of effective doses. This is consistent with an improved therapeutic index.
4. The compounds of the present invention, in particular CPT83, proved to be active by the oral route. Surprisingly, oral CPT83 is more active than topotecan, i.v. administered (with optimal treatment schedule).

As far as the industrial aspects of this invention are concerned, pharmaceutical compositions containing an effective amount of at least a compound of formula I as active ingredient in admixture with vehicles and excipients are a further object of the present invention.

Pharmaceutical compositions are prepared according to conventional methods well known in the art, for example as described in Remington's Pharmaceutical Sciences Handbook, Mack. Pub., N.Y., U.S.A.

Examples of pharmaceutical compositions are injectable compositions, such as solutions, suspensions emulsions in aqueous or non aqueous vehicle; enteral composition, such as capsules, tablets, pills, syrups, drinkable liquid formulations. Other pharmaceutical compositions compatible with the compunds of formula (I), such as controlled release formulations, are comprised in the present invention.

The dosage of the active ingredient in the pharmaceutical composition shall be determined by the person skilled in the art depending on the activity and pharmacokinetic characteristics of the active ingredient. The posology shall be decided by the physician on the grounds of the type of tumor to be treated, the conditions of the patient.

The compounds of the present invention can also be used in combination therapy with other antitumor drugs.

The following Examples further illustrate the invention.

EXAMPLE 1

20S-camptothecin-7-carbonitrile 1) 400 mg of the oxime of camptothecin-7-aldehyde (Sawada et al. Chem. Pharm. Bull. 39, 2572 (1991)), 102 mg of sodium formate and 15 ml of 99% formic acid are refluxed for 6 hrs. The solution is added with 150 ml of water and 50 ml of $CH_2Cl_2$, the two phases are separated, and the aqueous phase is extracted again 4 times. The organic extracts are evaporated, and the residue is chromatographed on silica gel Merck$^R$, with $CH_2Cl_2$—MeOH 96:4. The nitrile (300 mg) is obtained as a yellow solid, m.p. 263° C. Mass (M/e %): 374 (16), 373 (98), 344 (36), 329 (48), 314 (55), 301 (53), 300 (53), 273 (100).

$^1$H NMR (DMSO-$d_6$) 0.92 ($CH_3$), 1.92 ($CH_2$), 5.48, 5.51 ($CH_2$-5), 5.56 ($CH_2$-17), 6.62 (OH), 7.13 (CH-14), 8.02 (CH-11), 8.10 (CH-10), 8.30 (CH-9), 8.39 (CH-12).

2) 320 mg of camptothecin-7-aldehyde, 154 mg of $NH_2OH.HCl$, 578 mg of sodium formate and 20 ml of formic acid are refluxed 3 hrs, 60 mg of $NH_2OH.HCl$ are added, and the mixture refluxed 2 hrs. Water (90 ml) is added, and the mixture is extracted with $CH_2Cl_2$. The compound is recovered and purified as described above.

3) 500 mg of camptothecin N-oxide are refluxed with 0.86 ml of trimethylsilylcyanide and 0.32 ml of benzoyl peroxide in 45 ml of 1,1,2,2-tetrachloroethane for 12 hrs. The mixture is cooled and evaporated, and the residue chromatographed on silica gel Merck$^R$ with hexane-ethyl acetate 4:6 as eluent to give camptothecin-7-carbonitrile.

Starting from the suitable 10-substituted camptothecins, the following compounds were analogously prepared:

20S-10-hydroxycamptothecin-7-carbonitrile
20S-10-acetoxycamptothecin-7-carbonitrile
20S-10-methoxycamptothecin-7-carbonitrile
20S-10-methoxymethoxycamptothecin-7-carbonitrile
20S-10-ethoxycamptothecin-7-carbonitrile
20S-10-benzyloxycamptothecin-7-carbonitrile
20S-10-β-D-glycosyloxycamptothecin-7-carbonitrile
20S-camptothecin-7-yl-malononitrile
Ethyl 20S-camptothecin-7-yl-cyanoacetate

EXAMPLE 2

20S-camptothecin-7-carbamidoxime

A suspension of 60 mg of camptothecin-7-carbonitrile, 40 mg of hydroxylamine hydrochloride and 0.2 ml of triethylamine in 5 ml of absolute ethanol is refluxed 8 hrs, with addition of a further amount of 40 mg of $NH_2OH$.HCl and of 0.2 ml of $Et_3N$ after 4 hrs. The mixture is evaporated, taken up with water, filtered, and the precipitate chromatographed on silica gel Merck$^R$ with $CH_2Cl_2$—MeOH 9:1 to give camptbthecin-7-carbamidoxime.

The following compounds were analogously prepared:

20S-10-hydroxycamptothecin-7-carbamidoxime
20S-10-acetoxycamptothecin-7-carbamidoxime
20S-10-methoxycamptothecin-7-carbamidoxime

EXAMPLE 3

20S-7-amidinocamptothecin 100 mg of 20S-camptothecin-7-carbamidoxime in 10 ml of methanol are hydrogenated in the presence of 1 g of Nickel Raney catalyst under pressure of 50 atm and at the temperature of 70° C. for 5 hrs. Filtration of the catalyst, and evaporation gave 20S-7-amidinocamptothecin as a glassy solid.

The following compounds were analogously prepared:

20S-10-hydroxy-7-amidinocamptothecin
20S-10-acetoxy-7-amidinocamptothecin
20S-10-methoxy-7-amidinocamptothecin

EXAMPLE 4

20S-7-(2, 2-dicyanoethenyl)camptothecin 60 mg of camptothecin-7-aldehyde were refluxed 4 hrs. with 3 ml of malononitrile in 8 ml of 1,1,2,2,-tetrachloroethane and in the presence of 20 mg of LiBr. Cooling, filtration and chromatography on silica gel with ethyl acetate gave 20S-7-(2,2-dicyanoethenyl)camptothecin, as a glassy solid. Mass (M/e) 424, 380.

$^1$H NMR (DMSO-$d_6$) 0.85 ($CH_3$), 1.88 ($CH_2$), 5.38, ($CH_2$-5), 5.45 ($CH_2$-17), 6.56 (OH), 7.36 (CH-14), 7.82 (CH-11), 7.96 (CH-10), 8.18 (CH-9), 8.26 (CH-12), 9.30 (CH═).

The following compounds were analogously prepared:

20S-7-(2,2-dicyanoethenyl)-10-hydroxycamptothecin
20S-7-(2,2-dicyanoethenyl)-10-methoxycamptothecin
20S-7-(2,2-dicyanoethenyl)-10-ethoxycamptothecin
20S-7-((2-cyano-2-ethoxycarbonyl)ethenyl)camptothecin

EXAMPLE 5

20S-7-(2-nitro-1-hydroxyethyl)-camptothecin 150 mg of camptothecin, 0.05 ml of nitromethane, 0.01 ml of triethylamine in 3 ml of isopropanol were refluxed 10 hrs. Evaporation, treatment with dil. HCl and $CH_2Cl_2$ and chromatography of the extract with 4% methanol in $CH_2Cl_2$ gave 20S-7-(2-nitro-1-hydroxyethyl)camptothecin.

$^1$H NMR (DMSO-$d_6$) 0.80 ($CH_3$), 1.84 ($CH_2$), 4.90–5.05 ($CH_2$-7), 5.46, ($CH_2$-5), 5.54 ($CH_2$-17), 6.33 (CHOH), 6.56 (OH-16), 6.91 (CHOH), 7.33 (CH-14), 7.70 (CH-11), 7.82 (CH-10), 8.17 (CH-9), 8.20 (CH-12.

The following compounds were analogously prepared:

20S-7-(2-nitro-1-hydroxyethyl)-10-methoxycamptothecin
20S-7-(2-nitro-1-hydroxyethyl)-10-ethoxycamptothecin

EXAMPLE 6

20S-7-(2-nitroethenyl)-camptothecin 50 mg of 20S-7-(2-nitro-1-hydroxyethyl)-camptothecin in 5 ml of tetrahydrofuran were refluxed 1–2 hrs with 20 mg of p-toluenesulfonic acid or with 0.03 ml of trifluoroacetic acid to give 20S-7-(2-nitroethenyl) camptothecin as a yellow glassy solid.

The following compounds were analogously prepared:

20S-7-(2-nitroethenyl)-10-methoxycamptothecin
20S-7-(2-nitroethenyl)-10-ethoxycamptothecin

What is claimed is:

1. A compound of formula (I)

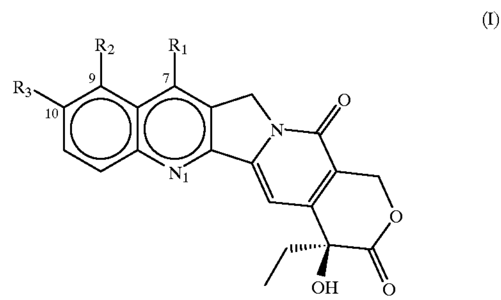

wherein:

$R_1$ is —CN, —CH(CN)—$R_4$, —CH═C(CN)—$R_4$, —$CH_2$—CH(CN)—$R_4$ —C(═NOH)—$NH_2$, —C(═NH)—$NH_2$, —CH═C($NO_2$)—$R_4$, —CH(CN)—$R_5$, —CH($CH_2NO_2$)—$R_5$; 5-tetrazolyl, 2-(4,5-dihydrooxazolyl), 1,2,4-oxadiazolin-3-yl-5-one;

$R_2$ is hydrogen;

$R_3$ is hydrogen, $OR_6$;

$R_4$ is hydrogen, $C_1$–$C_6$ linear or branched alkyl, CN, $COOR_7$;

$R_5$ is hydrogen, $OR_8$;

$R_6$ is hydrogen, $C_1$–$C_6$ linear or branched alkyl, ($C_6$–$C_{12}$) aryl ($C_1$–$C_4$) alkyl, ($C_1$–$C_4$) alkoxy ($C_1$–$C_4$) alkyl, ($C_1$–$C_4$) alkyl ($C_6$–$C_{12}$) aryl, ($C_6$–$C_{12}$) aryl ($C_2$–$C_4$) acyl, ($C_2$–$C_4$) acyl, AMINO ($C_1$–$C_4$) alkyl, amino ($C_2$–$C_4$) acyl, glycosyl;

$R_7$ is hydrogen, $C_1$–$C_6$ linear or branched alkyl, ($C_6$–$C_{12}$) aryl ($C_1$–$C_4$) alkyl, ($C_1$–$C_4$) alkoxy ($C_1$–$C_4$) alkyl, ($C_1$–$C_4$) alkyl ($C_6$–$C_{12}$) aryl;

$R_8$ has the same meanings of $R_6$, independently of the latter;

their $N_1$-oxides, their isomers, diastereoisomers, enantiomers and mixtures thereof.

2. A compound according to claim 1 in the form of a pharmaceutically acceptable salt.

3. $N_1$-oxide of a compound according to claim 1.

4. A compound according to claim 1, wherein $R_3$ is hydrogen.

5. A compound according to claim 1,wherein $R_3$ is $OR_6$ and $R_6$ is as above defined.

6. A compound according to claim 1, wherein $R_1$ is —CN, $R_2$ and $R_3$ are hydrogen.

7. A compound according to claim 1, wherein $R_1$ is —CH═C(CN)—$R_4$, wherein $R_4$ is CN, $R_2$ and $R_3$ are hydrogen.

8. A process for the preparation of a compound of claim 1, comprising:

a) the conversion of a compound of formula (II)

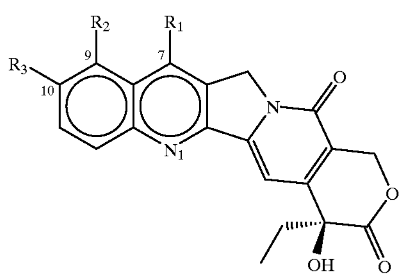

wherein $R_1$ is CHO, $R_2$ is hydrogen, $R_3$ has the same meanings as in formula (I), into the corresponding oxime, followed by the treatment with HCOOH/HCOONa to give the corresponding compounds of formula (I) wherein $R_1$ is —CN; and, if desired b) the treatment of the compound of formula (I) obtained in step a) with hydroxylamine to give the corresponding compounds of formula (I) wherein $R_1$ is —C(═NOH)—$NH_2$; and, if desired, c) catalytic hydrogenation of the compound of formula (I) obtained in step b) to give the corresponding compound of formula (I) wherein $R_1$ is —C(═NH)—$NH_2$; or, if desired, the transformation of the compound obtained in any one of the steps a) or b) or c) in the corresponding N1-oxide or a pharmaceutically acceptable salt.

9. A compound of formula (I)

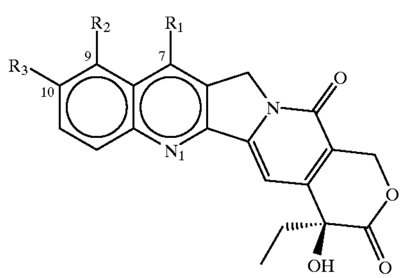

wherein $R_1$ is —CN, $R_2$ and $R_3$ are as above defined, as intermediate in step b) in the process of claim 8.

10. A compound of formula (I)

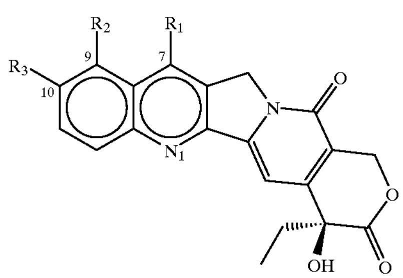

wherein $R_1$ is —CN, $R_2$ and $R_3$ are as above defined, as intermediate in a process for the preparation of compounds of claim 1, wherein $R_1$ is selected from the group consisting of —C(═NOH)—$NH_2$, —C(═NH)—$NH_2$, 2-(4,5-dihydroxazol-yl), 5-tetrazolyl.

11. A process for the preparation of a compound of claim 1, wherein R1 is selected from —CN or —CH(CN)—$R_4$, wherein $R_4$ is as above defined, comprising the reaction of camptothecin N-oxide with, respectively, one of potassium or trimethylsilyl cyanide, or the compound $R_4$—$CH_2$-CN, wherein $R_4$ is as above defined, and optional conversion in a pharmaceutically acceptable salt.

12. A process for the preparation of a compound of claim 1, wherein $R_1$ is —CH═C(CN)—$R_4$ or —$CH_2$—CH(CN)—$R_4$, wherein $R_4$ is as above defined, comprising the reaction of a compound of formula (II)

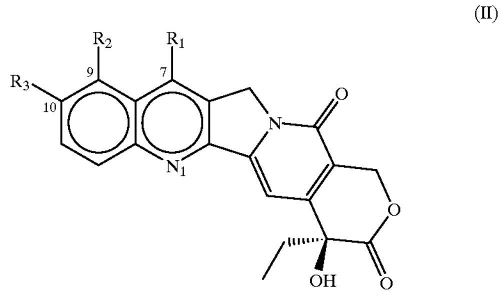

wherein $R_1$ is CHO, $R_2$ is hydrogen, $R_3$ has the same meanings as in formula (I), with the compound $R_4$—$CH_2$—CN, wherein $R_4$ is as above defined, to give the compound of formula (I) wherein $R_1$ is —CH═C(CN)—$R_4$ and, if desired hydrogenation to a compound of formula (I), wherein $R_1$ is —$CH_2$—CH(CN)—$R_4$, or the optional conversion in a pharmaceutically acceptable salt.

13. A process for the preparation of a compound of claim 1, wherein $R_1$ is selected from —CH(CN)—$R_4$, —CH($CH_2NO_2$)—$R_5$, wherein $R_4$ is as above defined, and $R_5$ is OH, comprising the reaction of a compound of formula (II)

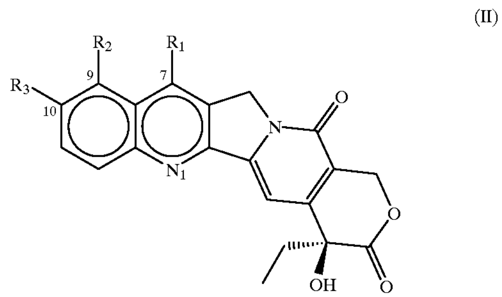

herein $R_1$ is CHO, $R_2$ is hydrogen, $R_3$ has the same meanings as in formula (I), with, respectively, one of potassium or sodium or trimethylsilyl cyanide, or nitromethane in the presence of an inorganic or organic base and optional conversion in a pharmaceutically acceptable salt.

14. A method for inhibiting the growth of NCI-H460 tumor cells in a mammal in need of said treatment which expresses high levels of topoisomerase I consisting essentially of the step of administering directly to the tumor an effective amount of a 20S-camptothecin derivative according to claim 1.

15. A pharmaceutical composition comprising as active ingredient an effective dose of a compound of claim 1 in admixture with pharmaceutical vehicles and excipients.

* * * * *